United States Patent [19]
Evans et al.

[11] Patent Number: 6,036,703
[45] Date of Patent: Mar. 14, 2000

[54] METHOD AND APPARATUS FOR ESTABLISHING ANASTOMOTIC PASSAGEWAYS

[75] Inventors: David K. Evans, Fishers, Ind.; Ronald J. Brinkerhoff, New Richmond, Ohio; Hal H. Katz, West Chester, Ohio; William J. Kraimer, Cincinnati, Ohio

[73] Assignee: Ethicon Endo-Surgery Inc., Cincinnati, Ohio

[21] Appl. No.: 09/245,513

[22] Filed: Feb. 5, 1999

Related U.S. Application Data

[60] Provisional application No. 60/073,884, Feb. 6, 1998.

[51] Int. Cl.$^7$ .................................................. A61B 17/00
[52] U.S. Cl. ............................................................ 606/153
[58] Field of Search ................................... 606/153, 152, 606/154, 155, 219, 151, 139

[56] References Cited

U.S. PATENT DOCUMENTS

| | | |
|---|---|---|
| 3,166,072 | 1/1965 | Sullivan, Jr. . |
| 4,214,586 | 7/1980 | Mericle .................................. 606/153 |
| 5,618,306 | 4/1997 | Roth et al. . |
| 5,695,504 | 12/1997 | Gifford, III et al. . |

FOREIGN PATENT DOCUMENTS

WO97/28745  8/1997  WIPO .

*Primary Examiner*—Michael Buiz
*Assistant Examiner*—Vikki Trinh
*Attorney, Agent, or Firm*—Woodard, Emhardt, Naughton, Moriarty & McNett Patent and Trademark Attorneys

[57] ABSTRACT

A system for establishing an anastomotic passageway between first and second structures within an animal, the first and second structures each having an intima-exposing opening comprises a first plate sized and configured for attachment to the opening of the first structure, the first plate including an attaching portion having means for gripping first structure at its opening, the first plate further including a coupling portion which is positioned exterior of the first structure when the first plate is attached to the first structure; a second plate sized and configured for attachment to the opening of the second structure, the second plate including an attaching portion having means for gripping the second structure at its opening, the second plate further including a coupling portion which is positioned exterior of the second structure when the second plate is attached to the second structure; and means for connecting the coupling portion of said first plate with the coupling portion of said second plate.

12 Claims, 14 Drawing Sheets

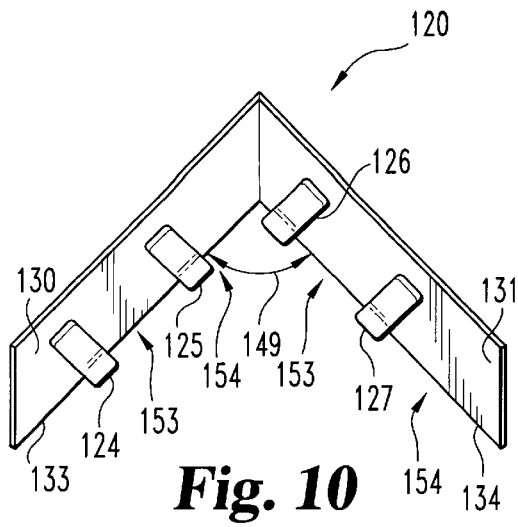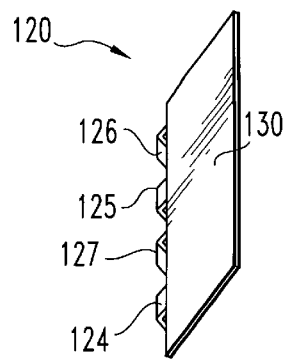
Fig. 10  Fig. 11
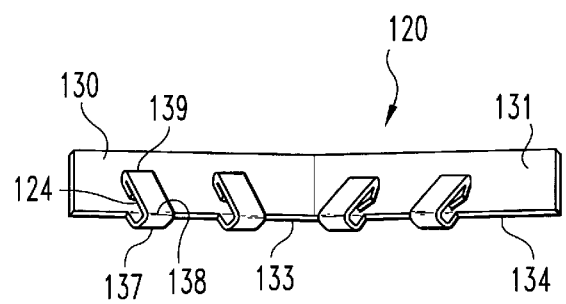
Fig. 12
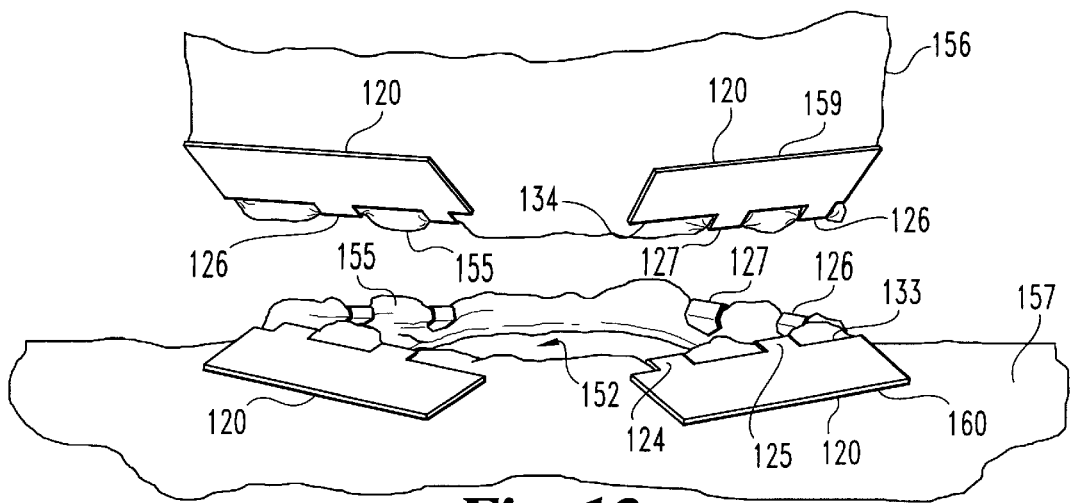
Fig. 13

METHOD AND APPARATUS FOR ESTABLISHING ANASTOMOTIC PASSAGEWAYS

REFERENCE TO RELATED APPLICATIONS

The present invention claims priority from my U.S. Provisional Application filed Feb. 6, 1998 and assigned Ser. No. 60/073,884.

FIELD OF THE INVENTION

The present invention relates to the field of tubular anastomoses, and specificlly to a method and apparatus for establishing anastomotic passageways in tubular vessels.

BACKGROUND OF THE INVENTION

Historically, CABG's (coronary artery bypass graft) have been hand sewn and the surgeon's skill and experience are truly tested in creating the arteriotomy, trimming the graft and placing the 20 or more sutures to create a patent anastomosis in vessels that are between one and four millimeters in diameter. Particular attention is paid to suture placement to (1) secure the intima to the vessel wall; (2) prevent the dislodgment of plaque or intimal flaps; (3) provide an intima-to-intima joint; (4) ensure that the flow channel proximal to the heel and toe portions of the joint remain open: and (5) make a leak-proof joint.

In practice, the heel and toe are the fixed points for the procedure and the side length of the anastomosis is adjusted to compensate for anatomical differences among patients. A disproportionate amount of the cardiovascular surgeon's skill and time is expended to accomplish the heel and toe of the anastomosis. For example, in a typical vascular graft, if the total length of the anastomotic joint is divided in thirds, the heel and toe portion represent about one-third of the length, but require about two-thirds of the time to complete. In the MIDCABG (compared to open) procedure, providing a patent anastomosis on a stabilized heart is more challenging due to the inherent motion of the vessels and the inherent difficulty and limited vision afforded by operating at the end of a stick. In addition, management of the heel and toe of an anastomosis is the more difficult and time-consuming portion of the entire procedure.

The literature is replete with a variety of types of fasteners (fittings, collars, stents, staples, clips, etc.) that can be used for tubular anastomosis. However, these fasteners have a number of undesirable characteristics such as being too large, being of fixed size or inflexible shape, being foreign body incompatible, having a tendency to create unacceptable flow disruption, and/or being difficult to use.

What is needed is a device that provides an improved system for creating a tubular anastomosis that is easier and more time efficient to use while not reducing the effectiveness or reliability of the procedure.

SUMMARY OF THE INVENTION

A system for establishing an anastomotic passageway between first and second structures within an animal, the first and second structures each defining an opening with exposed intima, opening, comprises a first plate sized and configured for attachment to the opening of the first structure, the first plate including an attaching portion having means for gripping the first structure at its opening, the first plate further including a coupling portion which is positioned exterior of the first structure when the first plate is attached to the first structure; a second plate sized and configured for attachment to the opening of the second structure, the second plate including an attaching portion having means for gripping the second structure at its opening, the second plate further including a coupling portion which is positioned exterior of the second structure when the second plate is attached to the second structure; and means for connecting the coupling portion of the first plate with the coupling portion of the second plate.

It is an object of the present invention to provide a device and method that more easily facilitates the connection of the heel and toe portions of a tubular anastomosis.

It is another object of the present invention to provide a device and method for creating an anastomosis with a leak-proof, intima-to-intima joint.

It is a further object of the present invention to provide a device and method for creating an anastomosis with minimal resultant flow disruption.

It is another object of the present invention to provide a device and method for creating an anastomosis where intimal flaps, vessel wall dissection and plaque separation or displacement are prevented.

Other objects and advantages of the present invention will become apparent from the following description of the preferred embodiment.

DESCRIPTION OF THE DRAWINGS

FIG. 10 is a top, plan view of an anastomotic plate 120 in accordance with preferred another embodiment of the present invention.

FIG. 11 is a side view of the anastomotic plate of FIG. 10.

FIG. 12 is a front view of the anastomotic plate 120 of FIG. 10.

FIG. 13 is a perspective view of anastomotic plates 120 of FIG. 10 shown clamped to a graft vessel and to a host vessel.

DESCRIPTION OF THE PREFERRED EMBODIMENT

Figure 1:
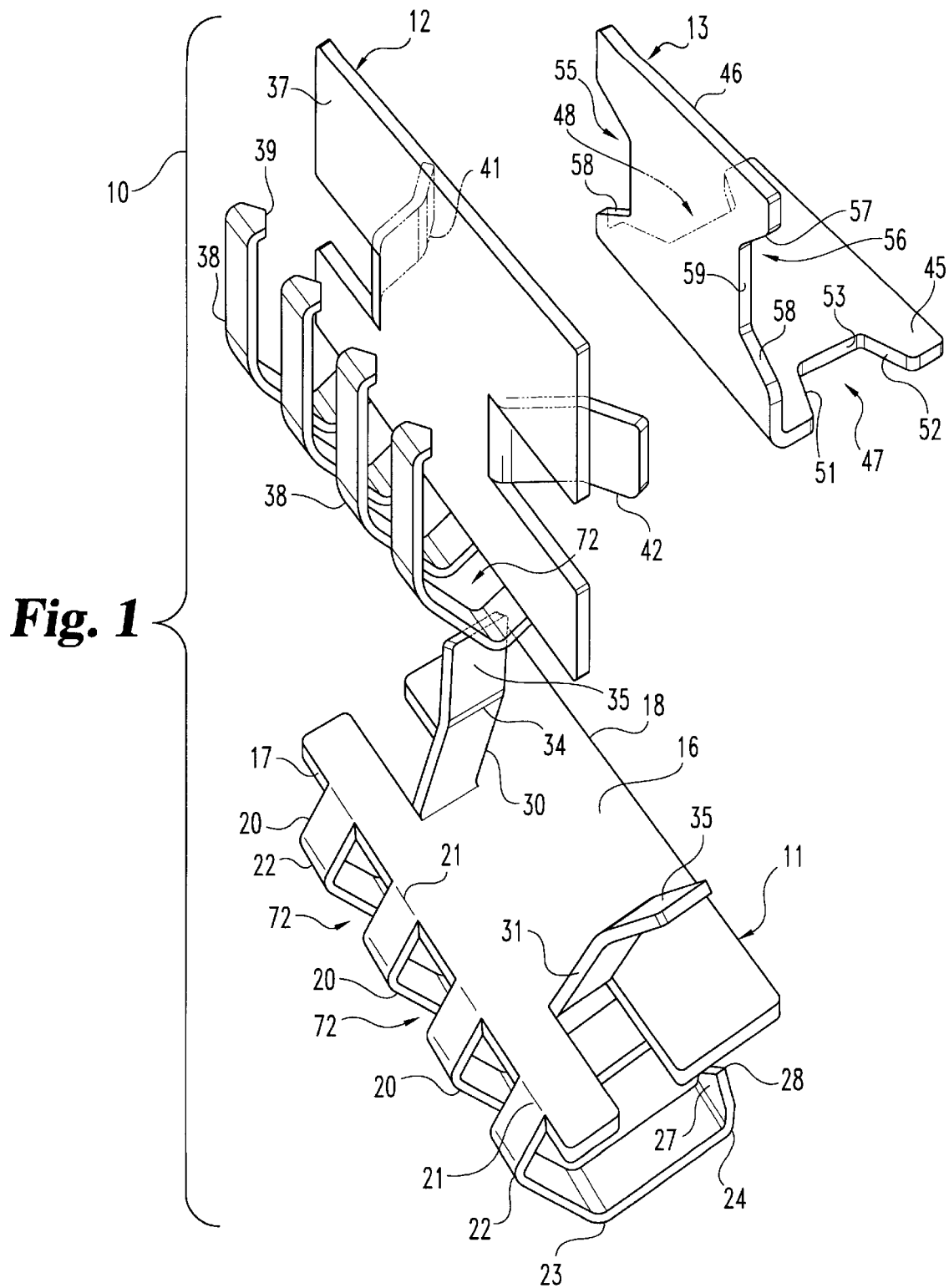
FIG. 1 is a perspective view of an anastomotic plate assembly 10 in accordance with one embodiment of the present invention.
Figure 2:
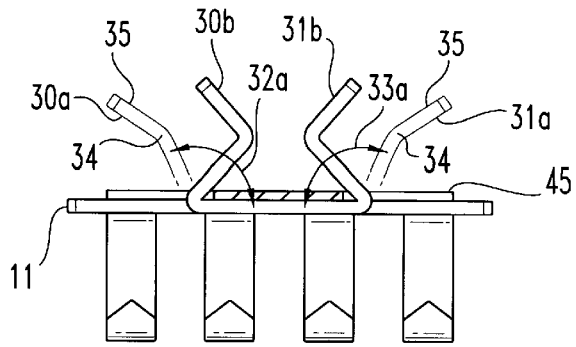
FIG. 2 is a rear view of the host plate 11 and connector 13 of the assembly of FIG. 1, shown in the assembled position and with a portion of connector 13 broken away for clarity.
Figure 3:
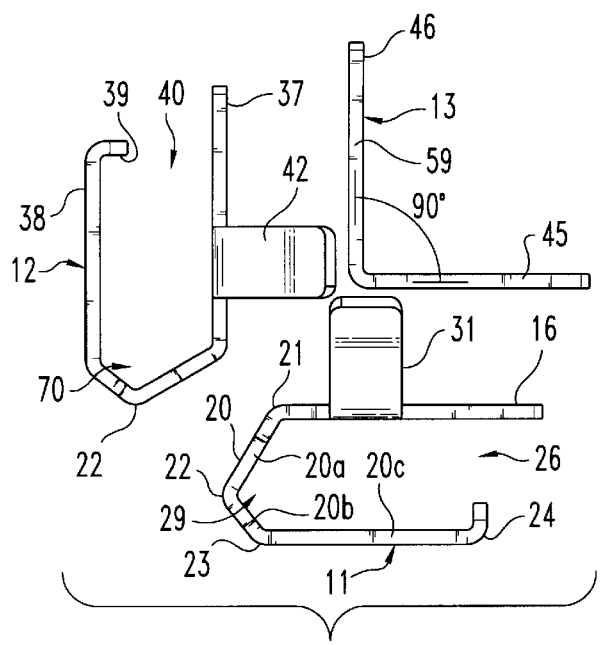
FIG. 3 is a side, exploded view of the anastomotic plate assembly 10 of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, and that any alterations or modifications in the illustrated device, and any further applications of the principles of the invention as illustrated therein are contemplated as would normally occur to one skilled in the art to which the invention relates.

While the descriptions herein describe the present invention as a method and apparatus for establishing anastomotic passageways (that is, establishing communication between two vessels or tubular structures), and while establishing anastomotic passageways is the primary intended use of the present invention, it is contemplated that the present invention is equally applicable to establishing a functional connection between any two structures within the body of an animal where such structures present intimal edges suitable to be conjoined.

Figure 4:
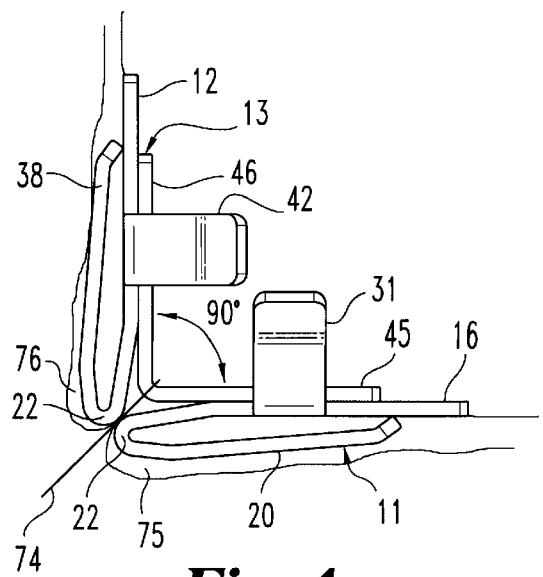
FIG. 4 is a side view of the anastomotic plate assembly 10 of FIG. 1 shown in the assembled and clamped position.

While the present invention contemplates a wide variety of configurations, the preferred embodiment is shown in FIGS. 14–25 and described herein. Referring now to FIGS. 1–4, there is shown a plate assembly 10 in accordance with one embodiment of the present invention. Plate assembly 10 includes a host plate 11, a graft plate 12, and a connector 13, each of which is made of a biocompatible metal such as stainless steel or titanium. Host plate 11 includes a generally flat base 16, with opposing, leading and trailing edges 17 and 18. Extending forwardly from leading edge 17 are a series of identical, deformable legs 20 which, through a series of bends 21–23, and in conjunction with base 16, define a generally "U" shaped trough 26. The distal most end of each leg 20 angles at 24 approximately 90° into trough 26 and tapers to a point 28 to define a tissue-gripping spike 27. As legs 20 are identical (or substantially so) to one another, reference may be made to just one leg 20, it being understood to refer equally to each leg 20 unless specified. Bends 21, 22, 23 and 24 are disposed about base 16 and leg 20 and at particular angles relative thereto to define leg sections 20a, 20b and 20c substantially as shown. Section 20a and 20b are each substantially shorter than section 20c and base 16, and the angle defined between sections 20a and 20b is more acute than the angles defined between base 16 and section 20a and between sections 20b and 20c. As described herein, this configuration permits leg 20 to be collapsed to a clamping position substantially as shown in FIG. 4. The region most inwardly into trough 26 and adjacent leg sections 20a and 20b is referred to as the throat 29 and is where the intimal layers of the vessels are positioned for mating contact upon creation of the anastomosis.

A pair of opposing, gripping flanges 30 and 31 are formed as cut-outs from base 16 and extend upwardly from base 16. Each flange 30 and 31 is slightly pre-bent at 34, as shown, so that the portions 35 of flanges 30 and 31, above the pre-bending lines 34, diverge from each other. Gripping flanges 30 and 31 are shown in their open position in FIG. 1 and are shown in their open position at 30a and 31a in FIG. 2. In the open position, the interior, opposing angles 32a and 33a of gripping flanges 30a and 31a are each 90 degrees or slightly greater than 90 degrees.

Graft plate 12 is substantially identical to host plate 11 and has a base 37, a series of legs 38, each having spikes 39 that extend toward the underside of base 37, a "U"-shaped trough 40 created between legs 38 and base 37, and a pair of upstanding, opposing gripping flanges 41 and 42.

Connector 13 is generally an "L"-shaped plate having a host plate connection leg 45 and a graft plate connection leg 46. Host plate connection leg 45 defines a pair of opposing, identical, but mirrored alignment recesses 47 and 48, as shown in FIG. 1. Recess 47 is defined more particularly by a pair of opposing, inwardly diverging guide edges 51 and 52 and an interconnecting central edge 53. Graft plate connection leg 46 likewise defines a pair of opposing, identical, but mirrored recesses 55 and 56 with guide edges 57 and 58 and an interconnecting central edge 59.

Figure 5:
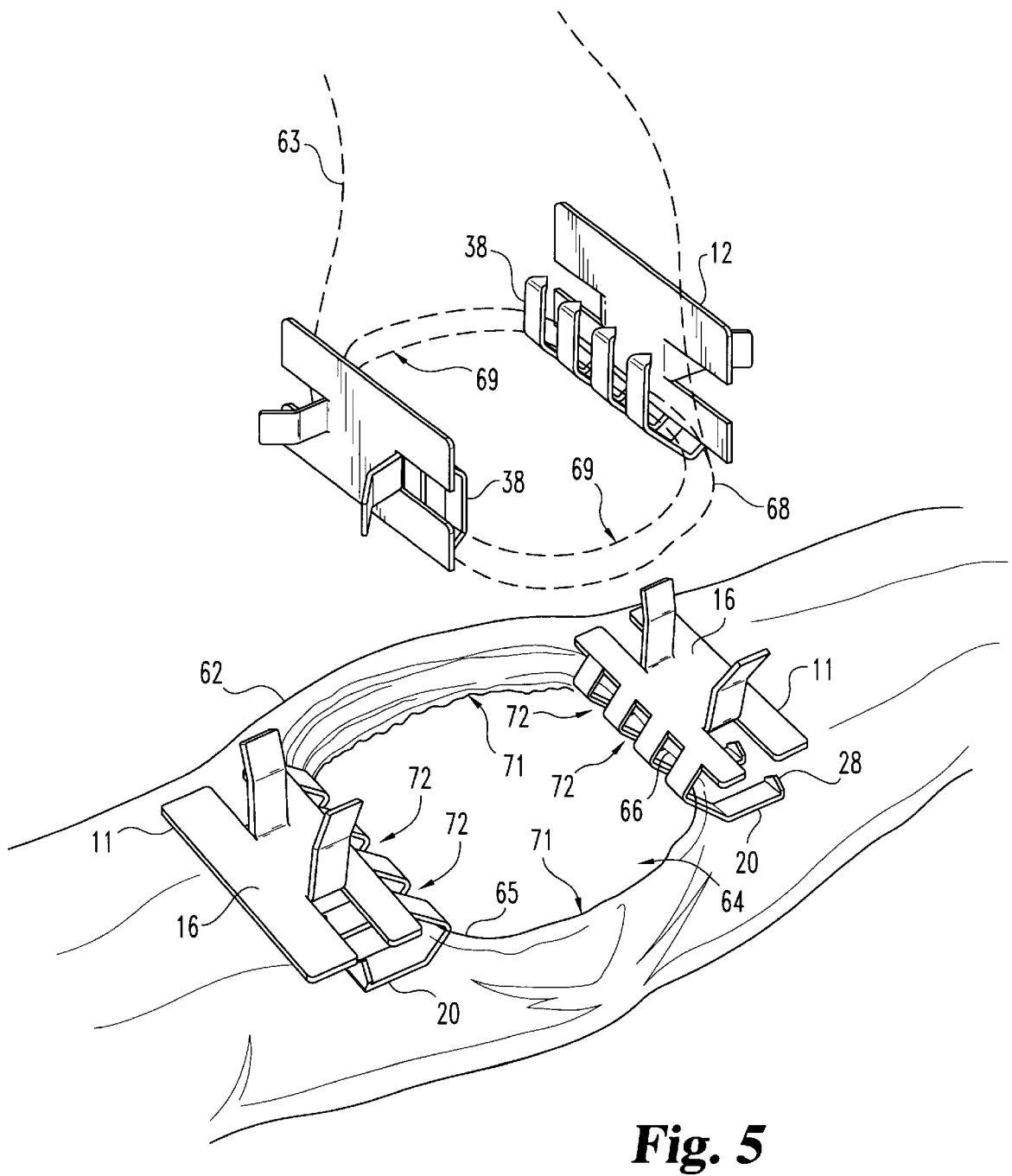
FIG. 5 is a perspective view of the anastomotic plates I I and 12 of FIG. 1 connected to host and graft vessels.

In use and referring to FIG. 5, to join a graft vessel 63 to host vessel 62 (IMA to LAD, for example) where the graft vessel 63 has been prepared for joining and the arteriotomy 64 has been created in the host vessel, the two host plates 11 are placed at each apex (heel and toe) of the arteriotomy 64 so that the V-shaped openings of each apex are kept open to ensure smooth flow in these transition zones. Each plate 11 is positioned so that the newly created edge 65 of the vessel wall is positioned into the trough 26 of each plate 11. Next, if the intimal layer has receded inwardly into the vessel due to the insult of being cut and handled, it is extracted from the vessel and into the throat 29 of trough 26. The legs 20, with spikes 27 designed to capture and fix the intimal layer to the vessel wall, are then bent toward base 16 by a suitable clamping tool or by hand to close trough 26, clamp the vessel wall firmly therewithin, and secure host plate 11 firmly on host vessel 62. In result, plate 11 is substantially affixed to the outside of the vessel in contact with the adventitial surface. Only the legs 20 are inside the vessel and are clamped tightly against and essentially concealed within the vessel wall. Flow within the lumen will thus be subject to minimal or no disruption.

Likewise, the two graft plates 12 are positioned 180° apart at the end 68 of the graft vessel 63, positioning the opposing sides of the vessel end 68 into troughs 40 of plates 12, extracting the intimal layer out into the throats 70 of troughs 40, and clamping legs 38 toward each base 37 to close troughs 40, clamp the vessel wall firmly therewithin, and secure graft plates 12 firmly onto the end 68 of graft vessel 63.

When legs 20 and 38 are fully deformed, they bury into the intima and the intima squishes out of the gaps 72 between each pair of adjacent legs 20 on plates 11 and between each pair of adjacent legs 38 on plates 12. As a result, intima is clearly presented along one edge of each of the plates 11 and 12 and, when re-endothelialization occurs, the legs will be concealed within the vessel wall and not disrupt flow.

To complete the heel and toe portions of the anastomosis, the respective plates on the host and graft vessels are joined to create a leakproof joint with intima-to-intima contact. In the present embodiment, plates 11 and 12 are joined to one another by connector 13. A connector 13 is first positioned against one of the graft plates 12 so that graft plate connection leg 46 rests against a corresponding base 37, with gripping flanges 41 and 42 extending through opposing alignment recesses 55 and 56. Because gripping flanges 41 and 42 diverge slightly as they extend away from base 37, connector 13 may be easily guided between flanges 41 and 42 and against base 37. Flanges 41 and 42 are then bent toward each other to firmly secure connector 13 to graft plate 12, as shown in FIG. 4. A second connector 13 is likewise affixed to the graft plate 12 on the opposite side of graft vessel 63. Graft vessel 63, with its graft plates 12 and corresponding connectors 13 firmly secured thereto, is then positioned toward the arteriotomy opening and opposing host plates 11 until the host plate connection leg 45 of each connector 13 sits upon the base 16 of a corresponding host plate 11 and so that the opposing gripping flanges 30 and 31 of each host plate 11 extend through the opposing alignment recesses 47 and 48. Gripping flanges 30 and 31 are then bent toward each other to the closed position to firmly affix each host plate 11 to its corresponding connector 13. To complete the connection of the graft vessel 63 to the host vessel 62, the surgeon sutures the remaining long portions 69 of the graft to the corresponding long portions 71 of the host. Alternatively, the remaining connection may be accomplished with staples, adhesives or other appropriate, biologically compatible methods.

Referring to FIG. 4, leg 45 forms approximately a 90° angle with leg 46 so that the graft vessel 63 will form roughly a 90° angle with the host vessel 62. It is contemplated that legs 45 and 46 could be at alternative angles to each other to create alternative angles between the graft and host vessels. It is also noted that host plate 11, graft plate 12 and connector 13 are configured so that when legs 20 and 38 are bent into their clamping positions and host plate 11 and graft plate 12 are connected with connector 13, the bends 22 of legs 20 are in mutual alignment and are in substantial abutment with the bends 22 of legs 38 which are also in substantial mutual alignment, and that the bends 22 of all of legs 20 and 38 are substantially in contact with a common plane 74 that approximately bisects the angle between connection legs 45 and 46. In use, with intima 75 of host vessel 62 and intima 76 of graft vessel 63 squishing out of the gaps 72 between their respective legs 20 and 38, bringing bends 22 into abutment should maximize the contact of intima 75 to intima 76 to create a leak-proof joint.

Alternative embodiments are contemplated wherein bends 22 do not come into abutment, but are slightly separated in assembly to account for anatomical variations among patients. Also, in the present configuration, there are four legs 20 and four legs 38. In assembly as shown in FIG. 4, the bends 22 of legs 20 and of legs 38 come into abutment at plane 74 in a one-to-one relationship. Alternative embodiments are contemplated wherein legs 20 and 38 are positioned, relative to their bases 16 and 27, respectively, so that, in assembly, the bends 22 of legs 38 of graft plate 12 align not with corresponding legs 20, but with the gaps 72. In this configuration, plates 11 and 12 may be configured so that, in assembly, bends 22 of legs 20 and 38 extend beyond plane 74 and overlap, thereby forcing the protruding intima 75 and 76 more tightly together.

The present invention operates, in part, by securing or clamping the intima (the inner layer) at the opening of the vessel to prevent dissection of the intimal layer and which thereby prevents an intimal flap from falling back into the vessel where it can block or impede flow within the vessel. To achieve such securement of the initima, it is contemplated, in this or other configurations, that there be at least one leg on each plate. That is, it is believed that the present invention will effectively secure the intima with just one leg 20, but it is preferred that there be at least two legs per plate, and that three per plate is optional, as will be described herein. The amount of legs per plate beyond two will depend, in part, upon the size of the vessels to be joined. The maximum number of legs is virtually unlimited. For example, technology may permit 50 legs per inch of width where such legs are still preferably about or ¼ or less of the distance between each leg. Furthermore, legs 20 of plate 11 may be shifted slightly to one side. Then the same plate 11 may be used for both the host and graft plate, and the bends 22 of legs 20 of the host plate will interfit with the bends 22 of legs 20 of the graft plate (that is, the bends 22 will automatically align with the gaps 72 between the legs 20 of the opposing plate), and thus there will be greater intima-to-intima contact. Examples of such interlacing of the legs is shown and described in alternative embodiments presented herein.

Figure 6:
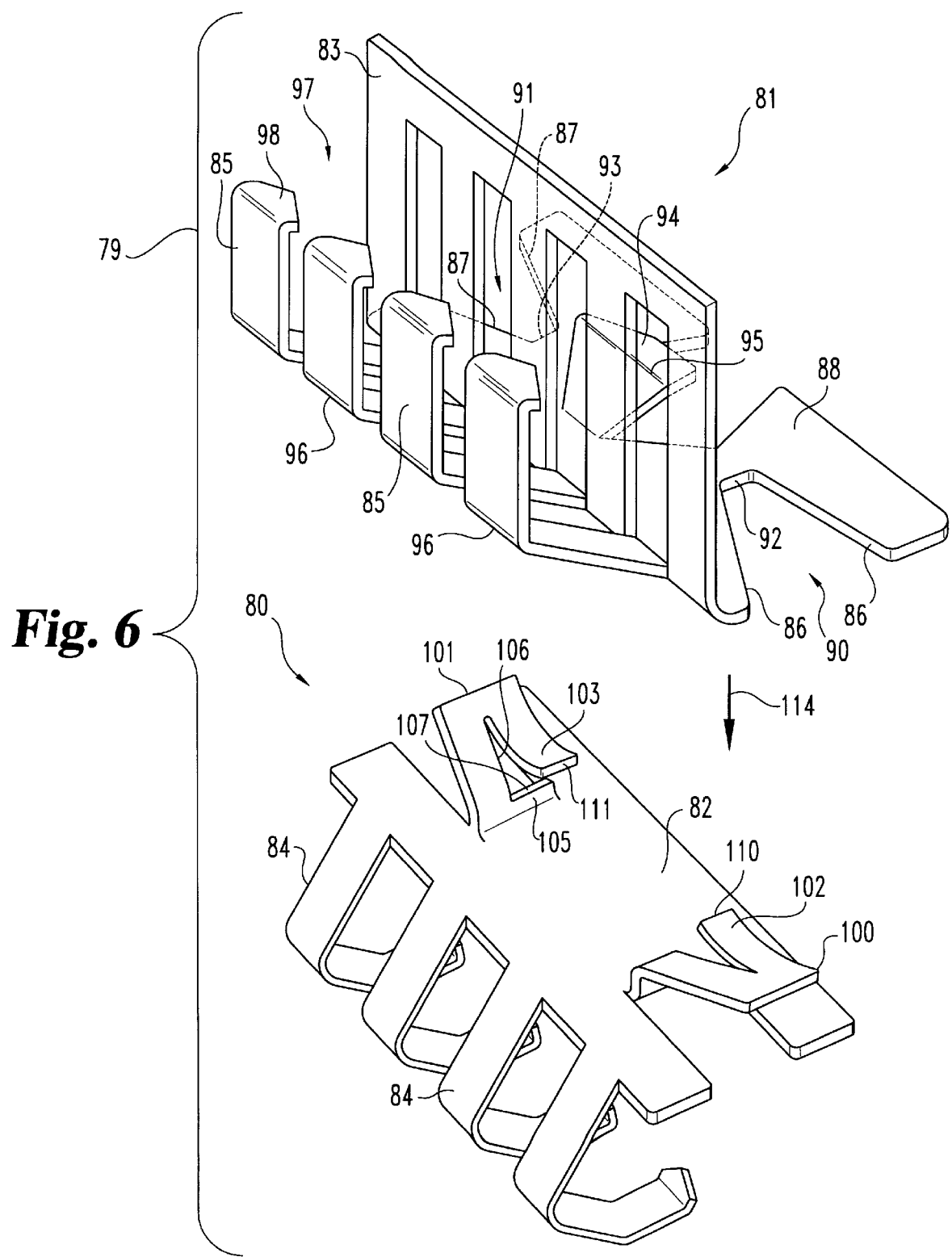
FIG. 6 is a perspective view of the host plate 80 and graft plate 81 of an anastomotic plate assembly 79 in accordance with another embodiment of the present invention.

Referring to another embodiment shown in FIG. 6, the connection of the host vessel to the graft vessels is simplified. There, an anastomotic plate assembly 79 includes a host plate 80 and graft plate 81 that are provided with means for directly connecting one to the other. More specifically, plates 80 and 81 each have a base 82 and 83, respectively, and have the same series of legs 84 and 85, respectively, extending therefrom in a configuration enabling them to be firmly affixed to a host and graft vessel. However, graft plate 81 has a generally L-shaped cross-section with one portion thereof forming a base 83 and the other portion, extending generally 90° therefrom, forming a connection arm 88. Connection arm 88 defines a pair of opposing recesses 90 and 91, with inwardly converging edges 86 and 87 and innermost connecting edges 92 and 93, respectively, recesses 90 and 91 being sized and positioned to receive flanges or a similar structure for locking engagement therewith. A gripping handle 94 is formed as a cut-out from arm 88, handle 94 angling upwardly therefrom and then angling downwardly from an intermediate bend at 95. Handle 94 is positioned midway between recesses 90 and 91 and facilitates graft plate 81 being gripped at handle 94 by a plier-like tool to manipulate plate 81 into its desired locking position as described herein.

Legs 85 of graft plate 81 are formed as cut-outs from base 83, as shown, and first extend away from connection arm 88 and base 83 at approximately a 45° angle relative to base 83. Each leg 85 then bends at 96 to extend generally parallel to base 83 to define a trough 97 between legs 85 and base 83. Like legs 20 of plates 38, each leg 85 then bends approximately 90° at its distal end and is pointed thereat to define spikes 98 that point toward base 83.

Figure 7:
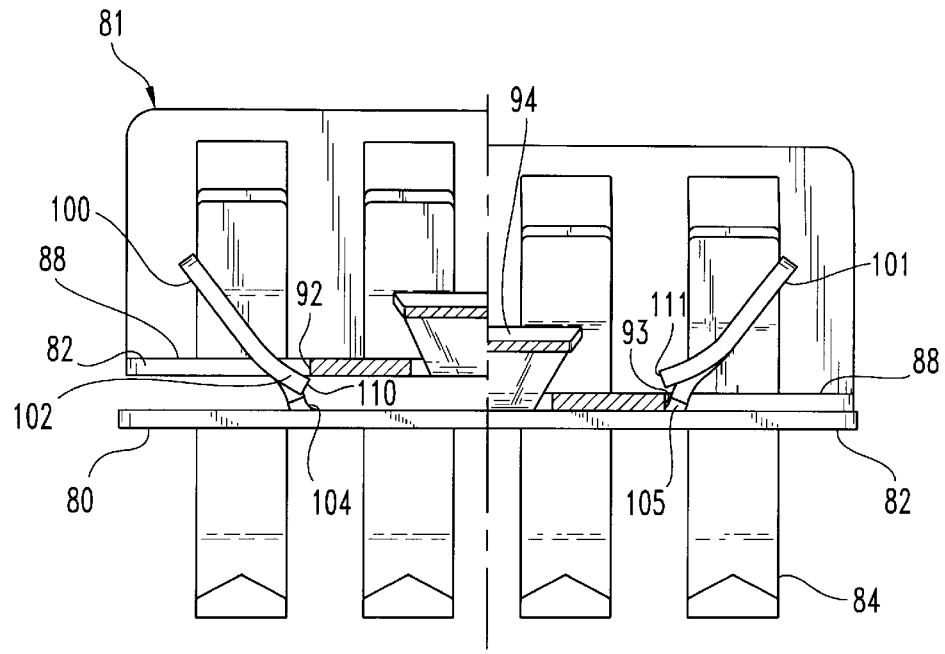
FIG. 7 is a rear view of the host and graft plates of FIG. 6 with the left half showing the host and graft plates nearly connected with one another and the right half showing the host and graft plates connected with one another.

Referring to base 82, as with gripping flanges 30 and 31 of graft plate 11 being formed as cut-outs from base 16 and extending upwardly therefrom, a pair of opposing locking flanges 100 and 101 are formed as generally rectangular cut-outs from base 82. Referring to FIGS. 6 and 7, each flange 100 and 101 extends upwardly at an angle of approximately 55° relative to base 82. Flanges 100 and 101 each include a locking tab 102 and 103, respectively, each of which is formed by cutting flanges 100 and 101 both longitudinally (at 106) and transversely (at 107), and then by bending the resulting tabs 102 and 103 along their length to form tabs 102 and 103 into a curved configuration, as shown, and to form stubs 104 and 105. The position of cuts 106 and 107, the degree to which tabs 102 and 103 are curvedly bent inwardly and away from the remaining structure of their flanges, and the angle that flanges 100 and 101 form with base 82 are selected: (1) so that stubs 104 and 105 extend somewhat upwardly from base 82 to help create a bounded gap between stubs 104 and 105 into which may be seated connection arm 88 between recesses 90 and 91, and (2) so that in the unstressed, rest position shown in FIG. 6 and on the right half of FIG. 7, the distance between the ends 110 and 111 of tabs 102 and 103, respectively, is less than the distance between innermost edges 92 and 93 of graft plate 81.

In use, and referring to FIGS. 6 and 7, the graft vessel 63 and host vessel 62 (IMA and LAD, for example) are prepared as described above for use of the plate assembly 10. As with application of plates 11 and 12, a pair of host plates 80 are positioned and firmly affixed at each apex of the arteriotomy by clamping legs 84 toward base 82. Likewise, a pair of graft plates 81 are affixed 180° apart and to the end of the graft vessel. The end of the graft vessel, with graft plates 81 firmly affixed thereto, is moved toward the host vessel and the corresponding, firmly affixed host plates 80, in the direction of arrow 114, so that locking flanges 100 and 101 extend up through recesses 90 and 91, respectfully. As graft plates 81 move toward host plates 80 and edges 86, 87 and/or 92 of arms 88 contact upwardly angled locking flanges 100 and/or 101, graft plates 81 and the graft vessel are moved into perfect alignment with host plates 80 and the arteriotomy opening (64 in FIG. 5). Because the distance between locking edges 92 and 93 of each connection arm 88 is greater than the distance between ends 110 and 111 of inwardly curved, but resilient locking tabs 102 and 103, connection arm 88 will eventually contact locking tabs 102 and 103 (left half of FIG. 7) and movement of graft plate 81 toward host plate 80 will be retarded. Additional pressure of that graft plate 81 toward its corresponding host plate 80 will downwardly deform one or both resilient locking tabs 102 and 103 until locking edges 92 and 93 of graft plate 81 pass beyond the ends 1 10 and 111 of tabs 102 and 103, whereupon, tabs 102 and 103 will spring back up to their rest position above and over connection arm 88 and graft plate 81 will be firmly locked in place against host plate 80, as shown in the right half of FIG. 7. Manipulation of graft plate 81 may be achieved by gripping the gripping handle 94 with a plier-type device or with one's own fingers.

While plate assembly 79 comprises a two-piece assembly whereby the connector 13 of assembly 10 is essentially built into graft plate 81, other embodiments are contemplated where the connector structure is built into the host plate or where the host and graft plates incorporate alternative structures for connecting to one another. Also contemplated to accommodate variations in vessel size are variations in plate size or adjustability of the size of the plates on site. Also, plates may have curved edges for a less abrupt heel or toe opening or to conform to the tubular shape of the vessel; complex curvatures of one or more of the plates may be incorporated also to accommodate variations in vessel configurations and size and to improve the transition zone. Also, the configuration of the graft and host plates may be made so that they connect with one another at angles between 0° and 180°. It is further contemplated that the deformable legs could be configured and affixed like hog rings or staples, and the spikes at the distal ends of the legs could be designed to pierce the intima and/or vessel wall.

While a number of geometries have been described herein to facilitate guidance upon connection of one plate to the other, other geometries are appropriate and contemplated by the present invention. Also, a number of locking features have been described to lock the host and graft plates together. The present invention contemplates other manners of connecting the host and graft plates together including but not limited to spring latches, Velcro®, sutures, bonding, screws, and staples. And while the embodiments presented herein include various handle structures for facilitating manipulation of the plates, other structures are also contemplated by the present invention.

Figure 8:
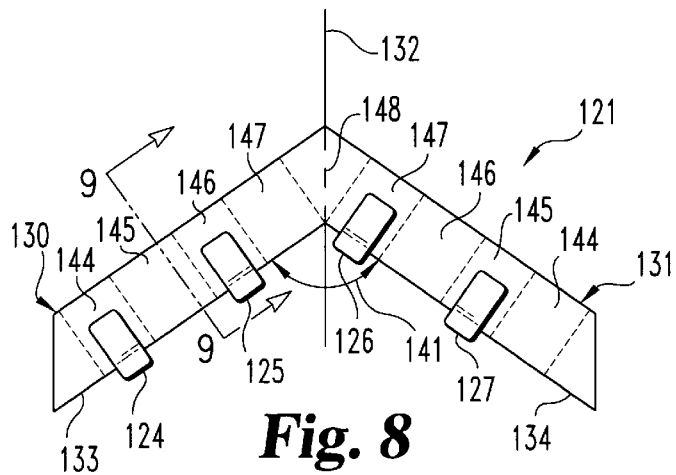
FIG. 8 is a top view of a planar, V-shaped plate 121 that, upon bending along line 148, will form the anastomotic plate 120 of FIG. 10.
Figure 9:
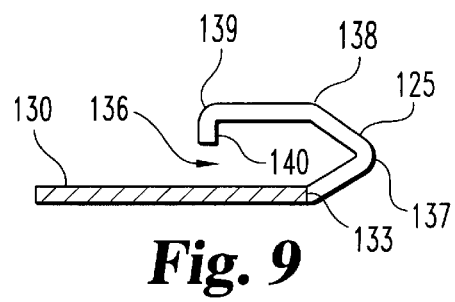
FIG. 9 is a side, cross-sectional view of plate 121 taken along the lines 9—9 of FIG. 8, and viewed in the direction of the arrows.

Referring to FIGS. 8–13, there is shown another embodiment of the present invention. Specifically, a plate assembly for creating an anastomotic passageway comprises four identical anastomotic plates 120 (FIG. 10) which can serve as both the host and graft plates. Like the host and graft plates 11 and 12 FIGS. 1–4, plate 120 has a base and a series of vessel engaging legs. The base of plate 120 initially comprises a single, planar and V-shaped plate member 121 (FIG. 8) having a series of vessel engaging legs 124–127. Plate member 121 is generally defined by a pair of parallelogram-shaped base legs 130 and 131 which are mirror images of each other about a plane 132 that is orthogonal to plate member 121. Similar to the legs 20 (FIG. 1) which extend forwardly and at an angle from the leading edge 17 of base 16 of plate 11, and down and back therefrom, under plate 16 to form a trough into which the edge 65 of vessel wall is disposed and clamped, legs 124–127 extend forwardly from leading edges 133 and 134 of base legs 130 and 131, respectively, and up (as viewed in FIG. 8) and back therefrom, over base legs 130 and 131 to form a trough 136 atop both base legs 130 and 131 into which the edge of a vessel wall may be disposed and clamped. Similar to each leg 20 of FIG. 1, leg 125 extends forwardly (FIG. 9) and at an angle from leading edge 133, then bends at 137 and 138 to form trough 136, and finally at 139 to form a spike 140. Each of legs 124, 126 and 127 extend in identical fashion from base legs 130 and 131, except that legs 124–127 are disposed in a non-symmetrical configuration along their respective legs 130 and 131. That is, as shown in FIG. 8, if each base leg 130 and 131 were divided into four, equally sized, rectangular quadrants 144–147 (quadrants 144–147 being mutually identical, and the quadrants 144–147 of leg 130 being identical to those on leg 131), then the first, outer vessel-engaging leg 124 of base leg 130 corresponds with the first quadrant 144, and the second, inner leg 125 corresponds with the third quadrant 146. But, on base leg 131, the first, outer vessel-engaging leg 127 corresponds with the second quadrant 145, and the second, inner vessel-engaging leg 126 corresponds with the fourth quadrant 147.

In the plan view of planar, V-shaped plate 121, leading edges 133 and 134 form an angle 141 of approximately 110°. To create the desired anastomotic plate 120 of the preferred embodiment, planar, V-shaped plate 121 is bent at line 148, so that parallelogram-shaped base legs 130 and 131 remain mirror images of each other (except for their vessel-engaging legs 124–127) about line 148 and plane 132, and until edges 133 and 134 form an angle 149 in plan view of approximately 90°, as shown in FIG. 10.

In use, a plate 120 is positioned relative to one apex (e.g. the heel) of the arteriotomy opening 152 until the edge of the vessel at the arteriotomy is positioned all the way into the troughs 136 corresponding to both base legs 130 and 131. Legs 124–127 are then squeezed to their clamped positions, firmly clamping the vessel wall therebetween. As shown in 10, it is desired that the width of vessel-engaging legs 124–127 be considerably less than the gap 153 between adjacent legs (e.g. 124 and 125) than the other adjacent open regions 154 along plate edges 133 and 134. Plate 120 is positioned so that the edge of the vessel wall at the arteriotomy is deeply pushed into trough 136 so that, upon clamped of legs 124–127 to their clamped positions, the intima (having been pulled out into the throat of trough 136 as appropriate and as described with plates 11 and 12 of FIG. 1) is squished out of gaps 153 and beyond legs 124–127 (at 155). An identically shaped plate 120 is similarly affixed to the opposing apex (e.g. the toe), and two more identically shaped plates 120 are similarly affixed 180° apart at and to the end of the graft vessel 156, all in the same manner so that the intima squishes out (at 155) of the gaps between adjacent legs. Because legs 124–127 are staggered, when a pair of the identical plates 120 are affixed to graft and host vessels 156 and 157, respectively, the base legs 130 and 131 are identically shaped and may be aligned perfectly, one over the other, to bring the graft vessel in perfect position over the arteriotomy, but each gap 153 of one plate 120 aligns with a vessel-engaging leg of the inverted plate 120 therebelow (or thereabove). Thus, when a plate 159 affixed to the graft vessel 156 is brought down and connected to the plate 160 of the host vessel 157, the gaps 153, with intima squishing out therefrom, of the upper and lower plates 159 and 160, are not in alignment, but rather align directly opposite a vessel-engaging leg. Nevertheless, because the width of each leg 124–127 is considerably less than that of the gaps and surrounding open regions 154, when the opposing (but otherwise identical) plates 159 and 160 are brought together and connected together, the intima squishes out so much that there is substantial intima-to-intima contact. In fact, the present configuration may be configured to create more intima-to-intima contact and a better seal between graft and host than the embodiments of FIGS. 1–7.

It should be understand that while certain angles for plate 120 have been described, other angles for the manufacture of plate 120 are contemplated. What is preferred is that the final angle 149 provide plate 120 with a desired flexibility of use and ease of connection to a vessel opening and it is believed that angle 149 at 90° and the configuration shown in FIGS. 10–13 provides such flexibility of use and ease of connection.

Referring to FIG. 13, another important aspect of the present embodiment is that the particular configuration presents both the graft and host plates from a single configuration, and when the graft vessel and its affixed plates 120 are positioned against the host vessel with its affixed plates 120, the leading edges 133 and 134 of one plate (159 for example, affixed to the graft vessel) come in planar contact with the leading edges 134 and 133, respectively, of the opposing plate (160, affixed to the graft). That is, all edges 133 and 134 are capable of abutting in a single plane, which will cause the graft vessel to be affixed to the host vessel at a 90° angle.

A number of connection means are disclosed herein for connection of a graft plate to a host plate, and any of those connections or other suitable connections would be appropriate to connect the plates 120 of a graft to the plates 120 of a host.

Figure 14:
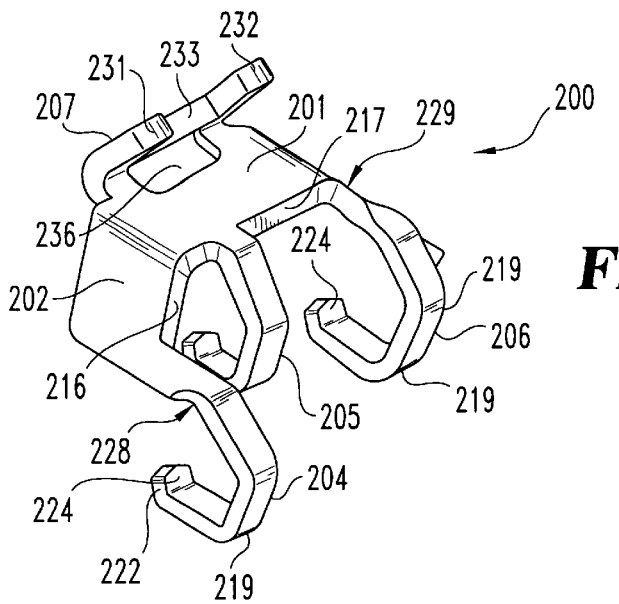
FIG. 14 is a front perspective view of anastomotic plate 200 in accordance with the preferred embodiment of the invention.
Figure 15:
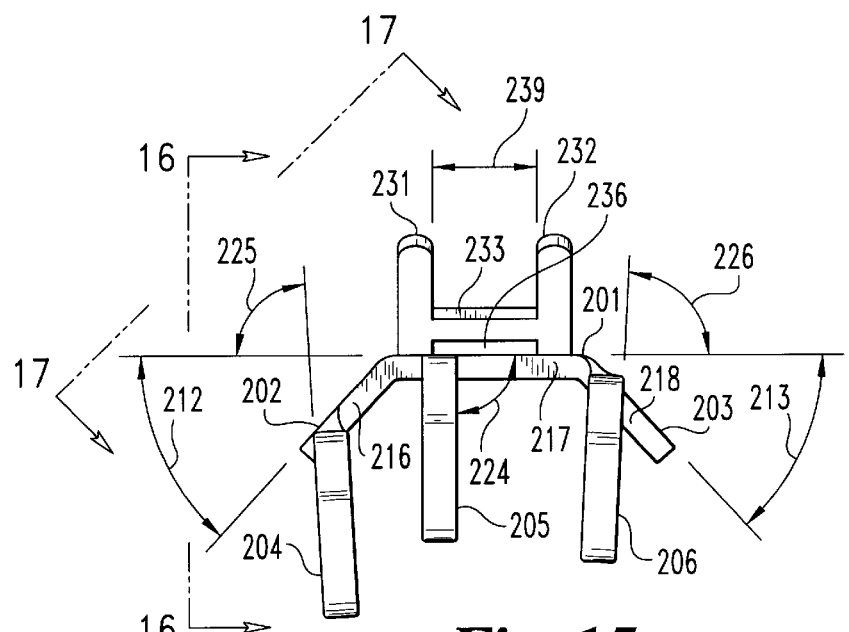
FIG. 15 is a front elevational view of the anastomotic plate 200 of FIG. 14.
Figure 16:
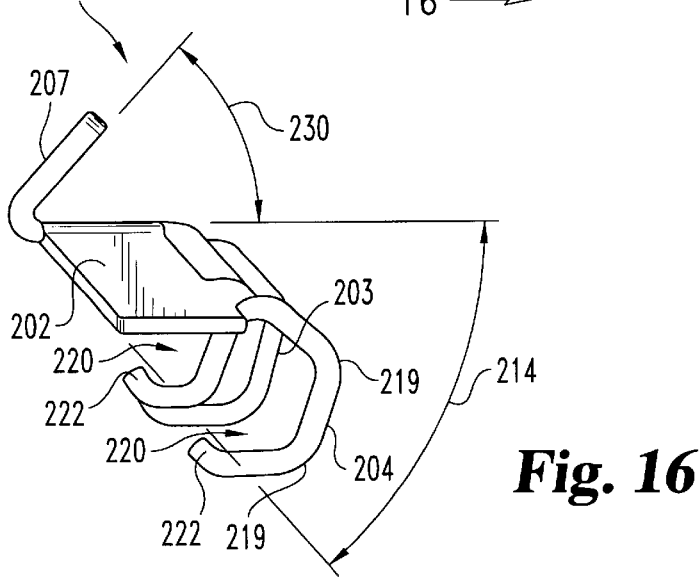
FIG. 16 is a side view of the anastomotic plate of FIG. 15 taken along the lines 16—16 and viewed in the direction of the arrows.
Figure 17:
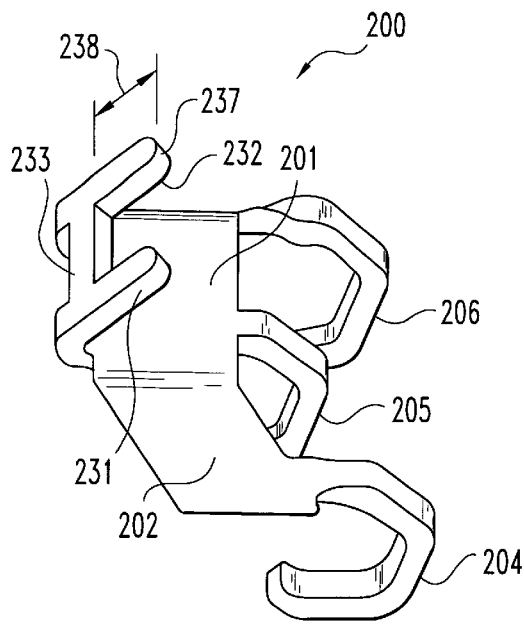
FIG. 17 is a perspective view of the anastomotic plate of FIG. 15 taken along the lines of 17—17 and viewed in the direction of the arrows.

Referring to FIGS. 14–24, there is shown the preferred embodiment of the present invention. Specifically, as with plates 120 of FIGS. 8–13, a plate assembly for creating an anastomotic passageway comprises four identical anastomotic plates 200 which can serve as both the host and graft plates. And, like the host and graft plates 11 and 12 of FIGS. 1–4, and like plate 120 of FIGS. 8 13, anastomotic plate 200 has a base and a series of vessel engaging legs. The base of anastomotic plate 200 includes a middle plate 201 and first and second wing plates 202 and 203. In addition to middle plate 201 and first and second wing plates 202 and 203, anastomotic plate 200 comprises three vessel engaging legs 204–206, and a mounting bracket 207. The configuration of anastomotic plate 200 is best represented by reference to FIGS. 14–18 where the dimensions and angles of the preferred embodiment of anastomotic plate 200 are believed to be substantially accurately depicted. In further explanation thereof, middle plate 201 is substantially planar and rectangular, and wing plates 202 and 203 have a substantially parallelogram shape, are also substantially planar, and are mirror images of each other about middle plate 201. As shown in FIGS. 15 and 16, the planes in which wing plates 202 and 203 reside form angles 212 and 213, respectively, with the plane of middle plate 201 of approximately 45°, and the acute interior angle 214 of each parallelogram shaped wing plate 202 and 203 is approximately 45°. These angles and the other shapes and dimensions of plate 200 may vary to accommodate varying shapes and sizes of the target host and graft vessel or body part.

Similar to the legs 124–127 of plate 120 of FIGS. 8–13, each leg 204–206 extends generally forwardly from leading edges 216–218, respectively, of wing, middle and wing plates 202, 201 and 203, respectively, and down (as viewed in FIG. 16) and rearwardly via bends 219 to form a trough 220 into which the edge of a vessel wall may be disposed and clamped. The most distal end 222 of each leg 204–206 is angled slightly into its corresponding trough 220 to form a spike 224, although the spikes 224 of legs 204–206 are not pointed as are spikes 140 of the embodiments of FIGS. 1–13. Also, as with legs 124–127, legs 204–206 are offset from the centerline (offset from center) of their respective plates 202, 201 and 203. Thus, as viewed in FIG. 15, each of legs 204–206 is disposed nearly all the way to the left side of their plates 202, 201 and 203. Furthermore, while leg 205 projects generally downwardly at an angle 224 of 90° relative to its middle plate 201, legs 204 and 206 do not project downwardly at angles of 90° relative to their respective plates 202 and 203. Instead, legs 204 and 206 project generally downwardly from their respective wing plates 202 and 203 at angles 225 and 226, respectively, of approximately 85°, with respect to middle plate 201 as shown, and with legs 204 and 206 angled slightly inwardly toward each other. To achieve this 85° angle between leg projection (of outer legs 204 and 206) and middle plate 201, where each leg 204 and 206 extends forwardly from a wing plate 202 and 203 that is angled 45° relative to middle plate 201, legs 204 and 206 are twisted at 228 and 229 near where they extend from their respective wing plates 202 and 203, respectively. Also, as shown in FIGS. 14 and 15, the width of each leg 204–206 is considerably less than the length of the its corresponding forward edge 216–219, which means that the width of each leg 204–206 is considerably less than the distance between each leg pair 204–205 and 205–206. It is desired that the width of each leg 204–206 be as small as possible while still providing sufficient clamping force to grip the vessel wall and while providing sufficient resistance to fracture or undesired bending. Consequently, there is a greater amount of intima exposed for contact and healing between the vessels to be joined.

Mounting bracket 207 extends rewardly from middle plate 201 and bends upwardly and forwardly therefrom at an angle 230 of approximately 45°, as shown. Mounting bracket 207 has a generally H-shaped configuration which includes first and second posts 231 and 232 and crossbar 233 extending therebetween. A generally rectangular opening 236 is thereby defined by posts 231 and 232 on the sides and by crossbar 233 and middle plate 201 on the top and bottom, respectively. The distance along each post 231 and 232 from crossbar 233 out to the tip 237 of each post is designated herein as the post length 238 (FIG. 17), and the distance between posts 231 and 232 is designated as the crossbar width 239 (FIG. 15). While each post 23 1 and 232 has a generally rectangular cross-section in a plane orthogonal to its axis, other configurations are contemplated.

Figure 18:
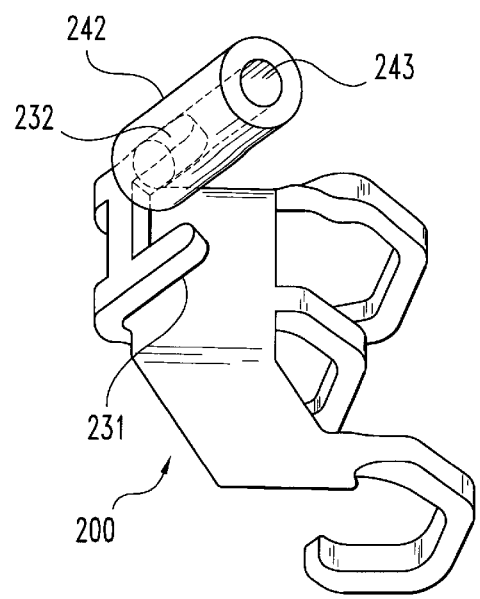
FIG. 18 is a perspective view of the anastomotic plate of FIG. 17 and shown with a joining tube 242 mounted to post 232.
Figure 22:
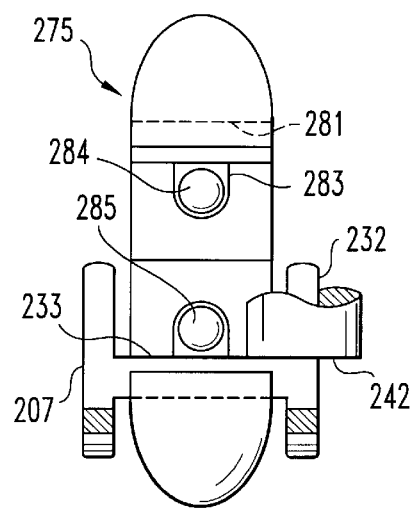
FIG. 22 is a front view of the distal end of the joining tool 275 of FIG. 21 taken along the lines 22—22 and viewed in the direction of the arrows.

Referring to FIG. 18, tube 242 has a lumen 243, is made of Teflon® or other appropriate and biocompatable material, and has a length that is approximately equal to or slightly more than twice post length 238. Tube 242 further has a wall thickness defined as one half the difference between the diameter of tube 242 and the diameter of lumen 243, and such wall thickness is less than one half of the crossbar width 239 by an amount greater than the diameter of pin 285 (FIG. 22). Prior to use, each anastomotic plate 200 is pre-assembled with one of the tubes 242 mounted to one post 232, whereby post 232 extends telescopically into the lumen 243. Because post length 238 is half or slightly less than half of tube length 242, when tube 242 is positioned all the way down over post 232 until it contacts crossbar 233, post 232 will extend just halfway or slightly less than halfway into lumen 243. For reasons which will become apparent herein, all anastomotic plates 200 are pre-assembled with the tube 242 on the same one of posts 231 and 232. Thus, for example, tubes 242 are only applied in pre-assembly to the right side post 232, as viewed in FIGS. 15 and 18, of all anastomotic plates 200. This preference may change to the other of the posts so long as there are corresponding changes to the forming tool (FIG. 20) to move its tubular portion 257 to the opposite side.

Figure 19:
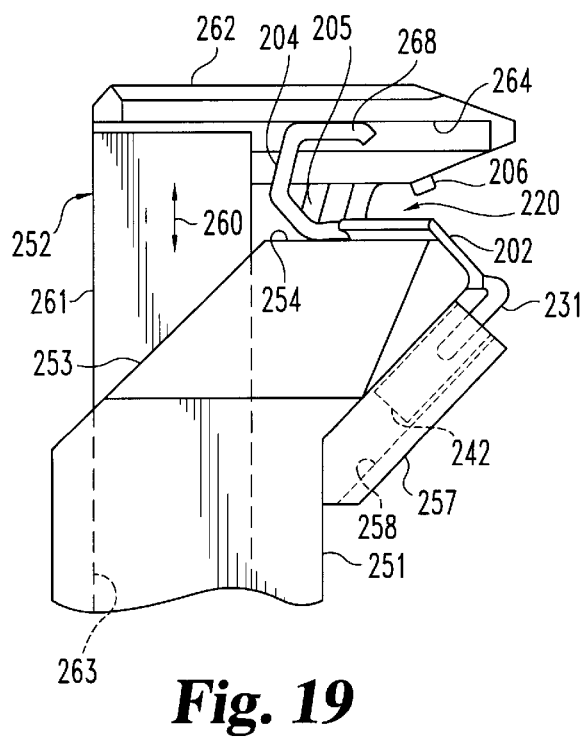
FIG. 19 is a side view of the distal or working end of a forming tool 250 for adjoining an anastoinotic plate 200 to the opening of a host or graft vessel.
Figure 20:
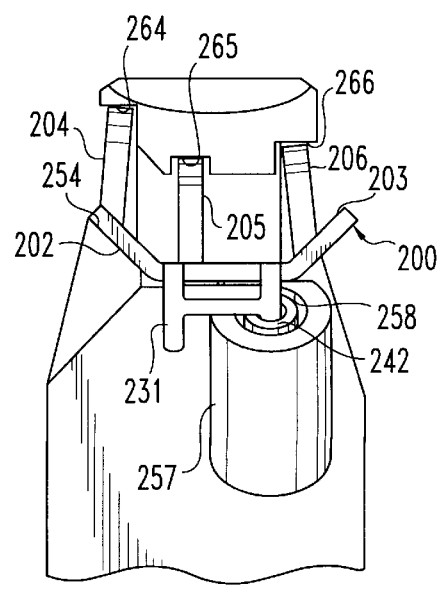
FIG. 20 is a front view of the distal or working end of forming tool 250 of FIG. 19.

Referring to FIGS. 19 and 20, there is shown the distal or working end of a forming tool 250 for adjoining an anastomotic plate 200 to the opening of a host or graft vessel. Forming tool 250 generally includes a tubular shaft 251 and a former 252. Shaft 251 includes a fixed anvil 253 at its distal end with an upper surface 259 of anvil 253 (as viewed in FIGS. 19 and 20) having a configuration that is complementary with the configuration of portions of an anastomotic plate 200 so that an anastomotic plate 200 may be seated upon anvil 253, as shown in FIGS. 19 and 20, whereby middle and wing plates 201–203 and portions of legs 204–206 are in superjacent contact with upper surface 254, and legs 204–206 project upwardly from upper surface 254, as shown. Shaft 251 further includes a forwardly and downwardly projecting tubular portion 257 (as viewed in FIG. 19), which defines a restraint hole 258 sized to receive $_{tube}$ 242 therein. The length of hole 258 is sufficient to receive the entire length of tube 242. Tubular portion 257 and its hole 258 are juxtaposed relative to anvil 253 so that when an anastomotic plate 200 is positioned atop anvil 253 as shown in FIGS. 19 and 20, its post 232 and tube 242 are securely positioned within hole 258. Anastomotic plate 200 is thus held in the proper positionment for being connected with the desired vessel.

Former 252 includes a rectangular cross-sectioned drive rod 261 and a forming head 262 fixedly connected with drive rod 261. Drive rod 261 extends through a complementary shaped passageway 263 in shaft 251 toward the proximal end of shaft 251 where it connects with a handle or similar assembly, as is well known in the art, to enable the user to manipulate such handle and cause drive rod 261 to telescopically reciprocate along path 260 relative to shaft 251. Drive rod 261 may be of any appropriate configuration as is known in the art for such application. Forming head 262 extends from drive rod 261 forwardly and defines three, generally planar die surfaces 264–266. Die surfaces 264–266 reside in different planes that are parallel to each other and orthogonal to the path 260 of reciprocation of drive rod 261. Dies surfaces 264–266 each have a width and are juxtapose relative to anvil 253 so that when an anastomotic plate 200 is positioned atop anvil 253, the distal ends 268 of each leg 204–206 align with and simultaneously engage a corresponding die surface 264–266 (as shown in FIG. 20).

In use, to apply or adjoin anastomotic plate 200 to one apex (e.g. the heel) of an arteriotomy opening, the anastomotic plate 200 is positioned in forming tool 250 as shown, it being stabilized upon fixed anvil 253 by the telescopic registration of post 232 and its tube 242 within restraint hole 258, the trigger handle or other appropriate activation mechanism at the proximal end (not shown) of forming tool 250 is activated slightly to bring forming head 262 closer to anvil 253 whereby die surfaces 264–266 lightly engage legs 204–206. Anastomotic plate 200 is thus in a mounted position in forming tool 250 and ready to be applied to the host or graft opening. Using forming tool 250, anastomotic plate 200 is maneuvered so that the edges of the vessel wall positioned within the troughs 220 of legs 204–206. For the graft vessel (like that shown in FIG. 3), this may be accomplished by using pickups (tweezer-like tool) to pull the vessel wall onto forming head 262 and into the trough 220. For the host vessel (like that shown in FIG. 3), this may be accomplished by maneuvering forming head right into the arteriotomy opening 64 whereby vessel wall is positioned into the trough 220. When in the desired position, the activation handle (not shown) at the proximal (not shown) of forming tool 250 is further activated to pull forming head 262 toward handle 253 along reciprocation path 260, whereby die surfaces 264–266 engage and deform legs 204–206 toward their corresponding plates 201–203 in a clamping configuration as described with respect to other embodiments herein. The activation handle (not shown) is released or moved in the opposite direction to raise forming head 262 away from handle 253 whereby forming tool 250 may be easily disengaged from the anastomotic plate 200 that is now firmly adjoined or clamped to the vessel wall.

Figure 21:
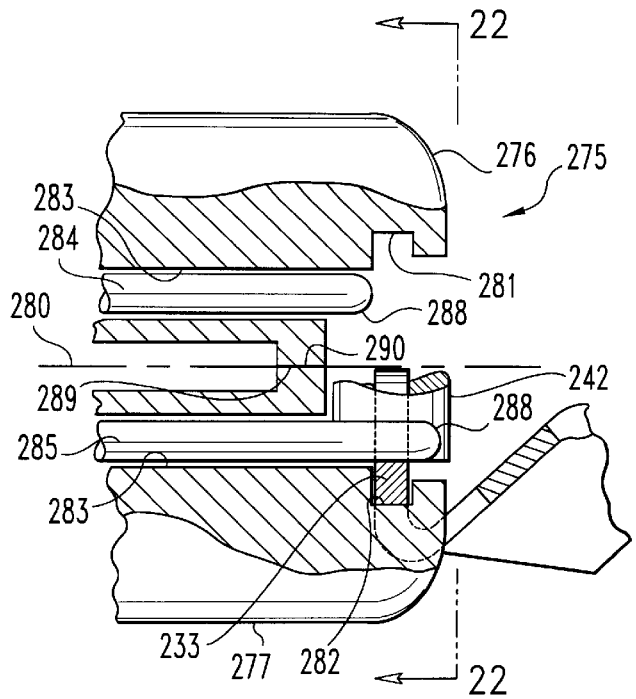
FIG. 21 is a side view, partially in section, of the distal end of a joining tool 275.

The manner of joining the anastomotic plate 200 of a graft vessel to a host vessel (or of connecting anastomotic plate 200 of one structure in the body having an exposed intimal edge to another structure in the body also having an exposed initmal edge), will now be described. Referring to FIGS. 21–25, there is shown the distal end of a joining tool 275, the joining tool 275 being for joining together the mounting brackets 207 of a mating pair of anastomotic plates 200 that have been clamped to two vessels within an animal body, such as the left anterior descending artery (LAD) and the internal mammary artery (IMA) not shown. At its distal end, joining tool 275 includes a pair of opposing upper and lower jaws 276 and 277, respectively, that are, in general, mirror images of each other. As viewed in FIG. 21, upper jaw 276 is shown in its plate release position, and lower jaw 277 is shown in its plate securement position. Jaws 276 and 277 are mounted at the distal ends of, or are integrally formed as the distal ends of the plier tips or pincers of a hemostat Thus, jaws 276 and 277 are disposed at the distal or working end of a tool (hereafter called a joining tool) that, by activation of a trigger or similar mechanism at the proximal end of such joining tool, pivots jaws 276 and 277 away from and toward center plane 280. The pivot point about which jaws 276 and 277 pivot is not shown herein, but is sufficiently remote (to the left and off the page of FIG. 21) from the most distal ends (to the right in FIG. 21), that jaws 276 and 277 essentially move away from and toward each other in virtually a straight line. Jaws 276 and 277 define opposing plate alignment slots 281 and 282, respectively, that are sized and shaped to receive the crossbar 233 of a mounting bracket 207. Jaws 276 and 277 define lateral passageways 283 that are sized to receive locking pins 284 and 285 for lateral, sliding reciprocation between a plate release condition and a plate gripping condition. In FIG. 21, upper jaw 276 is shown in the plate release condition whereby its pin 284 is retracted in passageway 283 to be sufficiently clear of slot 281 to enable the crossbar 233 of a mounting bracket 207 of an anastomotic plate 200 to be freely positioned within or removed from the slot 281. Lower jaw 277 is shown in the plate gripping condition whereby its pin 285 is extended forwardly from passageway 283 to pass beyond slot 282 and to trap a cross bar 233 of a mounting bracket 207 within the slot 282, as shown. Pins 284 and 285 may be remotely reciprocated between the retracted and extended positions by any appropriate mechanism or configuration as is known in the art. One example, but in no way intended to be limiting of such mechanism or configuration, includes said pins 284 and 285 being sufficiently stiff at their distal ends 288 to securely lock a crossbar 233 in slot 281 or 282, but themselves being sufficiently flexible to operate as a cable that can transmit axial tension and compression along its length, or being connected to the end of a cable that can transmit axial tension and compression along its length. Pulling or pushing such cable from the proximal end joining tool 275 causes the corresponding integral or connected pin 281 or 282 to retract or extend, respectively. The width of jaws 276 and 277, at least at a certain portion of the distal end thereof, is less than the crossbar length 239. Jaws 276 and 277 define traval stops 289 and 290 that engage each other when jaws 276 and 277 are closed to the desired position and prevent jaws 276 and 277 from coming any closer together.

In use, with anastomotic plates 200 clamped to the desired positions at the graft and host vessels, joining tool 275 is maneuvered so that the crossbar 233 one of the anastomotic plates 200 on the graft vessel is positioned in an alignment slot 282, and the corresponding locking pin 285 is telescopically extended to the plate gripping position, as shown in FIGS. 21 and 22. Joining tool 275 is then further maneuvered so that crossbar 233 of the anastomotic plate 200 connected at the mating position on the host vessel is positioned in slot 281 of the mating jaw 276, and locking pin 284 is extending to the plate gripping position. With the desired plate pair now firmly held in opposing jaws 276 and 277, the post 231 of each plate 200 is substantially coaxially aligned with the post 232 of the opposing plate 200. Since each plate 200 comes pre-assembled with a tube 242 coaxially mounted to its post 232, then plate 200 of jaw 276 has a tube 242 that is aligned to receive post 231 of the plate 200 of opposing jaw 277, and plate 200 of jaw 277 has a tube 242 that is aligned to receive post 231 of the plate 200 of opposing jaw 276. The user then closes jaws 276 and 277 together whereby posts 231 are forced into the open lumen of the opposing tubes. When jaws 276 and 277 are fully closed, defined by stops 289 and 290 coming in contact with each other, the posts 231 of each plate 200 have been snugly positioned within one end of the opposing tube 242, and as the post 232 of the opposing plate is snugly positioned in the opposite end each tube 242, the opposing plates of the host and graft vessels are firmly connected with each other, thus the host and graft vessels are firmly connected with each.

Figure 24:
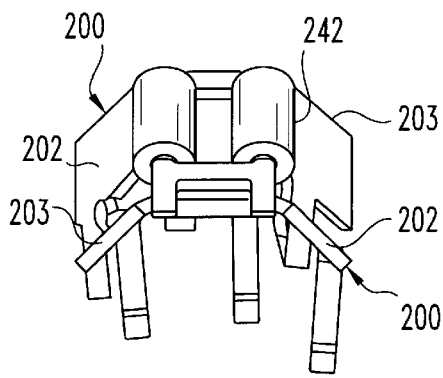
FIG. 24 is a perspective view of a pair of anastomotic plates 200, not connected with a structure in the body, but shown joined together by joining tubes 242.
Figure 23:
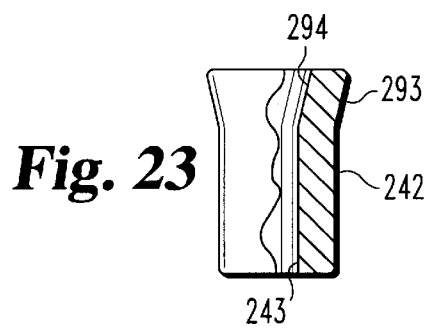
FIG. 23 is a side view, partially in cross-section, of a joining tube 242.
Figure 25:
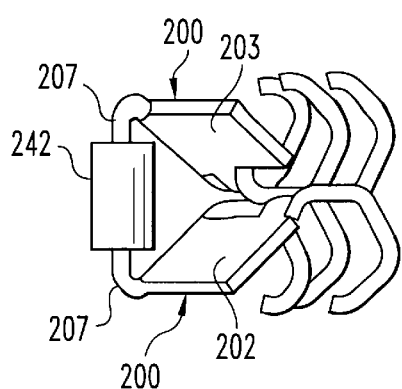
FIG. 25 is side view of the pair of anastomotic plates 200 joined by a pair of joining tubes 242 of FIG. 24.
Figure 26:
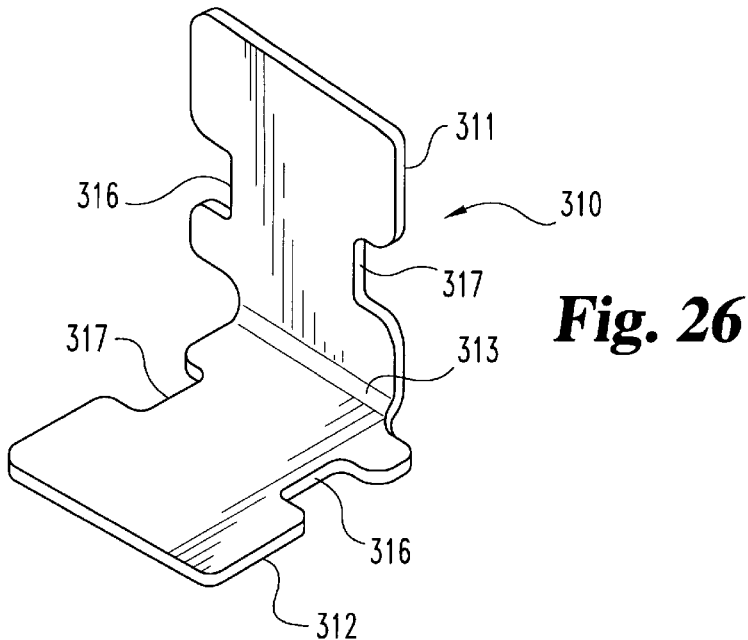
FIG. 26 is a perspective view of a connector 310 of another embodiment of the present invention.
Figure 27:
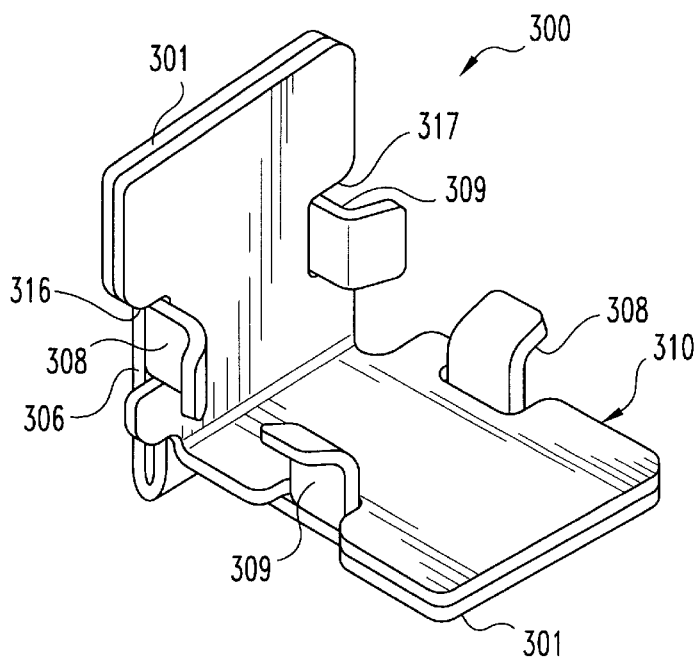
FIG. 27 is a rear perspective view of a pair of anastomotic plates 301 shown in the clamped condition and joined together by the connector 310 of FIG. 26.
Figure 28:
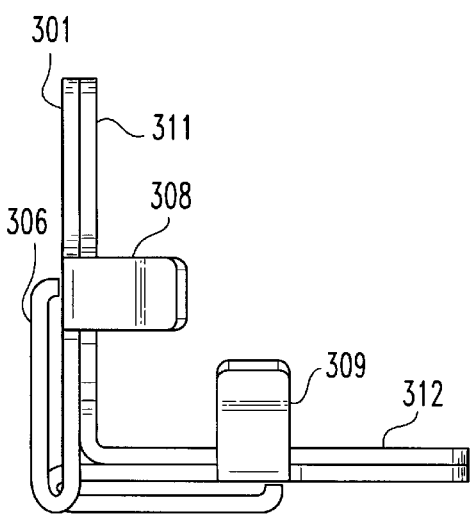
FIG. 28 is a side, elevational view of the plates 301 and connector 310 of FIG. 27.
Figure 29:
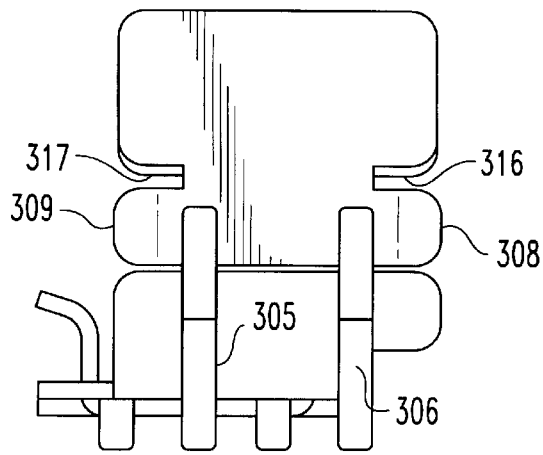
FIG. 29 is a front view of the anastomotic plates 301 and connector 310 of FIG. 27.
Figure 30:
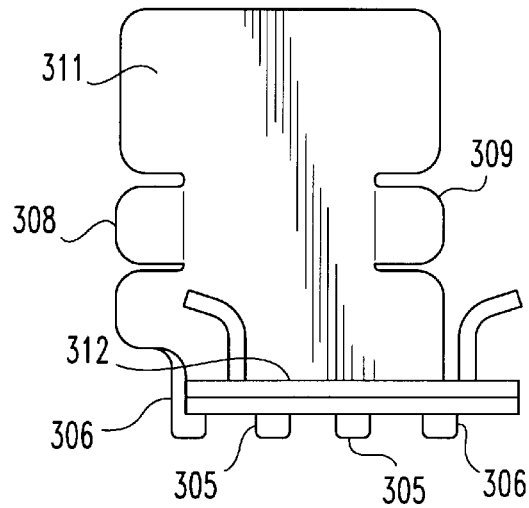
FIG. 30 is rear view of the anastomotic plates 301 and connector 310 of FIG. 27.
Figure 31:
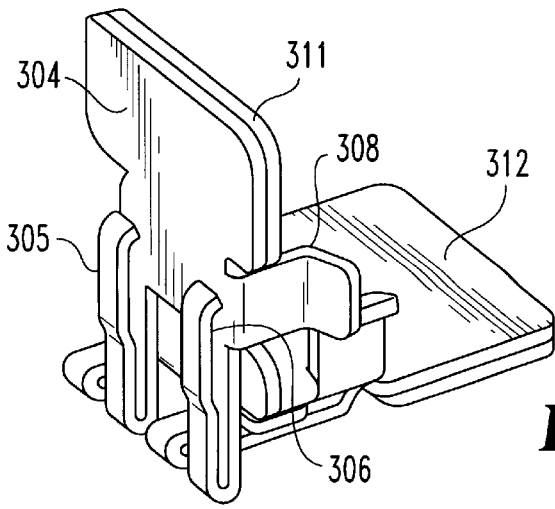
FIG. 31 is a front perspective view of the anastomotic plates 301 and connector 310 of FIG. 27.

FIGS. 24 and 25 show a pair of anastomotic plates 200 connected by tubes 242. FIG. 23 shows a tube 242 with one end 293, and specifically one end 294 of the lumen 243, slightly flared. This makes it easier for the user to align and cause the posts 23 1 to enter the lumens 243 of the opposing tubes when joining tool 275 is closed.

Referring now to FIGS. 26–31, there is shown another embodiment of the present invention. Like the anastomotic plate 120 of FIG. 10, and plate 200 of FIG. 14, plate 301 is configured to serve as both a host plate and a graft plate. Plate 301 generally includes a base 304 (FIG. 31) at least two deformable legs 305 and 306 and a pair of gripping flanges 308 and 309. A connector 310 includes first and second connector legs 311 and 312 that are identical with each other but in reverse orientation about there joint at 313 each connector leg defines a left and right alignment recess 316 and 317. Recesses 316 and 317 of one leg 311 are offset the recesses 316 and 317 of the other connector leg 312. Thus, when a plate 301 is locked to connector 311 whereby gripping flanges 308 and 309 extend through recesses 316 and 317 of plate 11, and another plate 301 is similarly connected with the second connector leg 312 whereby its gripping flanges 308 and 309 extend through recesses 316 and 317, the deformable legs 305 and 306 of the two now mechanically connected plates 301 interlace with each other, as seen if FIGS. 29–31.

Figure 32:
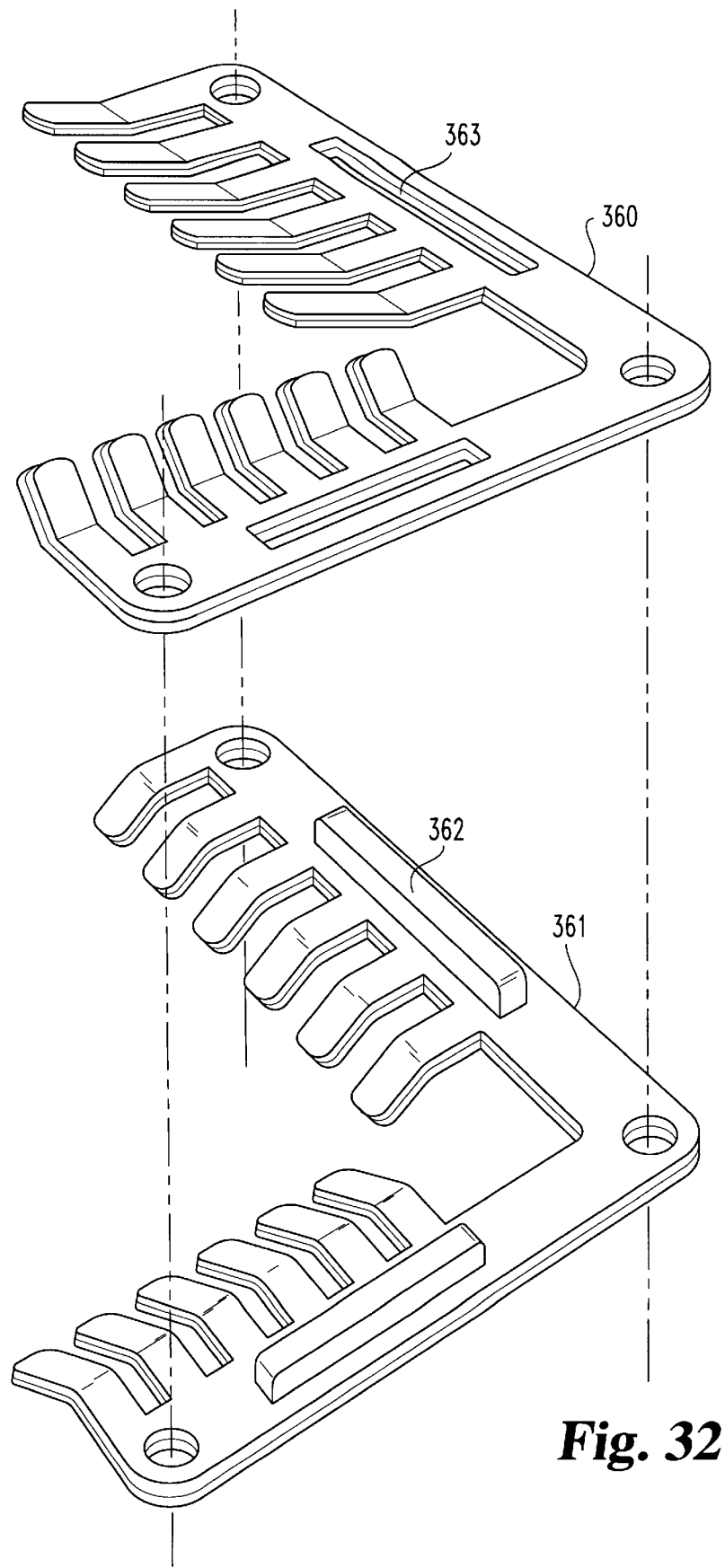
FIGS. 32–34 are views of additional embodiments of the present invention.
Figure 33:
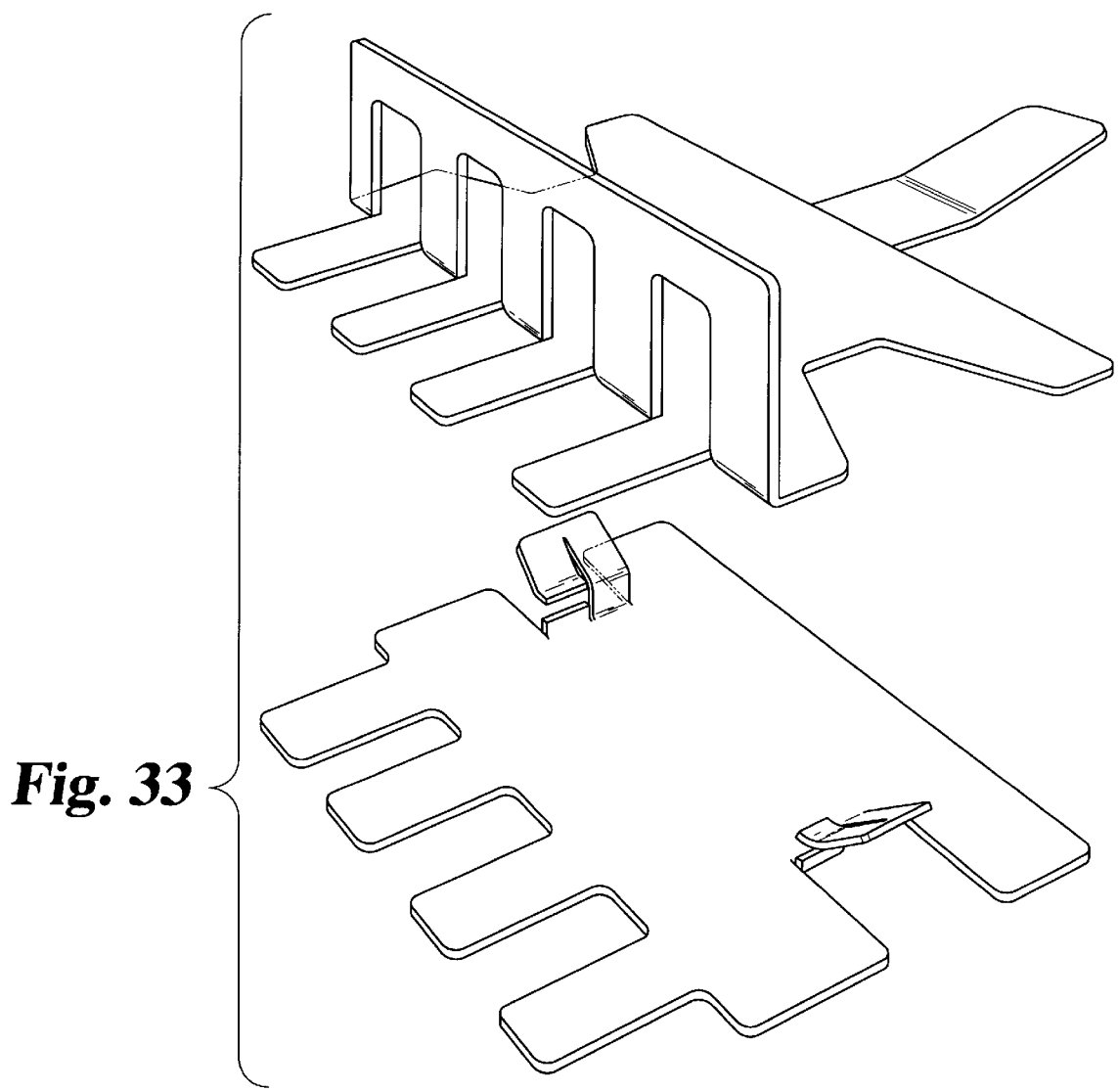
Figure 34:
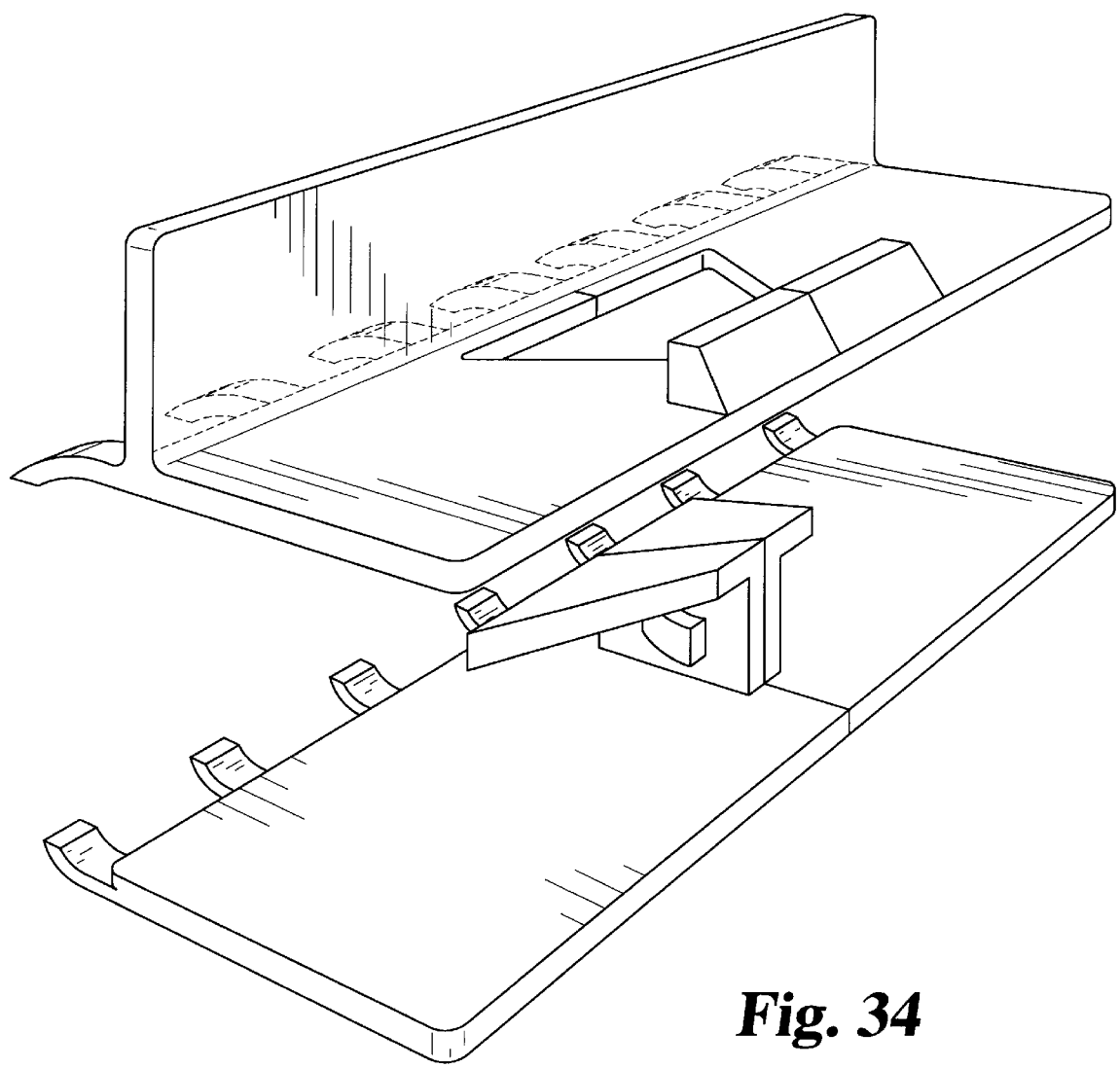

Referring to FIGS. 32–34, there are shown other embodiments of graft and host plates. In FIG. 32, the plates 360 and 361 are V-shaped to connect with and maintain the V-shaped configuration of the heel and toe of the arteriotomy. Plates 360 and 361 also include an upstanding post 362 and corresponding slot 363 for improved alignment of graft vessel to host vessel.

Each group of deformable legs extending from the plates of the embodiments disclosed herein have generally been disclosed to be identical. However, it is contemplated that the legs may vary from one another to achieve a desired purpose or adapt to a particular anatomical structure. The present invention further contemplates means other than the deformable legs extending from the plate bases to affix the plates to their respective vessels.

It is further contemplated that, while the embodiments presented herein have focused on a MIDCABG anastomosis, the invention contemplates application to other tubular anastomosis procedures including synthetic grafts. In the case of a synthetic graft, it is contemplated that the graft could be supplied with the graft plate already connected or physically incorporated with the graft material.

It is noted that the present invention not only provides a very effective method for mechanically joining together two intimal layers, but it also enables such joining for very small structures. For example, in one embodiment, anastomotic plates 200 and their associate forming tool 250 and joining tool 275 are sized to perform an anastomosis on vessels having a diameter of 1 mm and up.

Other embodiments are contemplated wherein the plates and/or connectors are made of a thermoplastic material that could be positioned at the vessel opening and then deformed with the application of heat and external deformation forces. Such material would be capable of taking a permanent set so that, upon removal of the heat, the material retains the deformed clamped or gripping configuration. Other materials as they are developed or available are also contemplated which, for example, have a memory so that they may be deformed by the application of heat or cold, placed in position at the vessel opening, and upon removal of the heat or cold, such material remembers its shape and returns to that shape, clamping the vessel and/or securing itself to another component of the anastomoses system. The present invention further contemplates a structure of a plate assembly where the plate (and/or connector) has a predetermined gripping and connecting configuration, but that such plate (and/or connector) may be mechanically deformed as by bending. Upon release of an external deformation force (without the need for applying heat or cold), the plate (and/or connector) returns to its gripping or securing configuration. It should also be understood that the "plate" of the present invention does not have to comprise a single unitary piece. It may comprise two or more pieces so long as it secures the intima at the opening of the vessel.

While the invention has been illustrated and described in detail in the drawings and foregoing description, the same is to be considered as illustrated and not restrictive in character, it being understood that only the preferred embodiment has been shown and described and that all changes and modifications that come within the spirit of the invention are desired to be protected.

What is claimed is:

1. A system for establishing an anastomotic passageway between first and second structures within the body of an animal, the first and second structures each defining an opening with exposed intima, the system comprising:

a first plate sized and configured for attachment to the intima of the first structure, said first plate including an attaching portion having means for gripping the first structure at its intima, said first plate further including a coupling portion which is positioned exterior of the first structure when said first plate is attached to the first structure;

a second plate sized and configured for attachment to the intima of the second structure said second plate including an attaching portion having means for gripping the second structure at its intima, said second plate further including a coupling portion which is positioned exterior of the second structure when said second plate is attached to the second structure; and means for connecting the coupling portion of said first plate with the coupling portion of said second plate.

2. The system for establishing an anastomotic passageway between first and second structures within an animal of claim 1 wherein the attaching portion of each of said first and second plates includes a base and a portion connected with the base for extending interior of the body and engaging the intima of the body.

3. The system for establishing an anastomotic passageway between first and second structures within an animal of claim 2 wherein the attaching portion of each of said first and second plates include a plurality of legs extending from the base.

4. The system for establishing an anastomotic passageway between first and second structures within an animal of claim 3 wherein each of said first and second plates has an open position whereby the base and the legs extend therefrom together to define a trough sized to receive therein a portion of the structure at the opening.

5. The system for establishing an anastomotic passageway between first and second structures within an animal of claim 4 wherein the legs are deformable between the open position and a clamped position in which the structure is gripped by the attaching portions.

6. The system for establishing an anastomotic passageway between first and second structures within an animal of claim 5 wherein the legs of each of said first and second plates include ends which are sized and configured to be extended into the structure and to engage with the intima therein.

7. The system for establishing an anastomotic passageway between first and second structures within an animal of claim 6 wherein the end of each leg is configured with a pointed spike to grip the intima of the structures.

8. The system for establishing an anastomotic passageway between first and second structures within an animal of claim 1 wherein said connecting means includes a connector having a first means for connecting with the coupling portion of said first plate and a second means for connecting with the coupling portion of said second plate to couple said first plate with said second plate.

9. The system for establishing an anastomotic passageway between first and second structures within an animal of claim 1 wherein said plates and connecting means are sized and configured to establish the anastomotic passageway and wherein the first structure is a vessel and the second body is an organ.

10. The system for establishing an anastomotic passageway between first and second structures within an animal of claim 1 wherein said plates and connecting means are sized and configured to establish the anastomotic passageway and wherein the first structure is a vessel and the second structure is a vessel.

11. The system for establishing an anastomotic passageway between first and second structures within an animal of claim 10 wherein the first structure is the left anterior descending artery (LAD) and the second structure is the internal mammary artery (IMA).

12. The system for establishing an anastomotic passageway between first and second structures within an animal of claim 1 said first plate is identical to said second plate.

* * * * *